United States Patent
Hänni et al.

(10) Patent No.: US 9,687,258 B2
(45) Date of Patent: Jun. 27, 2017

(54) AIMING DEVICE

(75) Inventors: Markus Hänni, Davos (CH); Peter Toggwiler, Davos Frauenkirch (CH); Norbert Suhm, Basel (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 2024 days.

(21) Appl. No.: 12/089,006

(22) PCT Filed: Oct. 5, 2006

(86) PCT No.: PCT/CH2006/000545
§ 371 (c)(1),
(2), (4) Date: Jun. 9, 2008

(87) PCT Pub. No.: WO2007/041880
PCT Pub. Date: Apr. 19, 2007

(65) Prior Publication Data
US 2009/0299416 A1 Dec. 3, 2009

(30) Foreign Application Priority Data

Oct. 10, 2005 (DE) .................... 20 2005 015 975 U

(51) Int. Cl.
| A61B 17/17 | (2006.01) |
| A61B 17/15 | (2006.01) |
| A61B 17/16 | (2006.01) |
| A61B 90/00 | (2016.01) |
| A61B 34/20 | (2016.01) |

(52) U.S. Cl.
CPC ............ *A61B 17/17* (2013.01); *A61B 17/151* (2013.01); *A61B 17/1668* (2013.01); *A61B 17/1697* (2013.01); *A61B 17/1703* (2013.01); *A61B 17/175* (2013.01); *A61B 17/1725* (2013.01); *A61B 17/1732* (2013.01); *A61B 34/20* (2016.02); *A61B 2090/3983* (2016.02)

(58) Field of Classification Search
USPC .......................................... 606/96, 205, 324
See application file for complete search history.

(56) References Cited

U.S. PATENT DOCUMENTS

| 2,181,746 A | * | 11/1939 | Siebrandt ........................ 606/96 |
| 2,291,413 A | * | 7/1942 | Siebrandt ..................... 606/103 |
| 2,531,734 A | * | 11/1950 | Hopkins ........................ 606/97 |
| 3,626,513 A | * | 12/1971 | Pytlak ...................... 408/115 R |
| 4,444,180 A | * | 4/1984 | Schneider et al. .............. 606/96 |
| 5,133,715 A | * | 7/1992 | Lenzo ............................ 606/60 |

(Continued)

FOREIGN PATENT DOCUMENTS

| CN | 2258055 | 7/1997 |
| WO | 2004/096068 | 11/2004 |
| WO | 2005/112805 | 12/2005 |

OTHER PUBLICATIONS

Albee F. H., Bone Surgery with Machine Tools, Apr. 1936, Scientific American, pp. 178-181.*

*Primary Examiner* — David Bates
(74) *Attorney, Agent, or Firm* — Fay Kaplun & Marcin, LLP

(57) ABSTRACT

An aiming device for insertion of a Kirschner-wire to treat a target bone, comprises an aiming block permitting placement of a Kirschner-wire against the target bone and a forceps connected to the aiming block, the forceps being configured to clamp to the target bone.

11 Claims, 4 Drawing Sheets

(56) References Cited

U.S. PATENT DOCUMENTS

| | | | |
|---|---|---|---|
| 5,403,321 A | * | 4/1995 | DiMarco .................. 606/96 |
| 6,010,508 A | | 1/2000 | Bradley |
| 6,010,509 A | | 1/2000 | Delgado et al. |
| 2003/0208122 A1 | | 11/2003 | Melkent et al. |

* cited by examiner

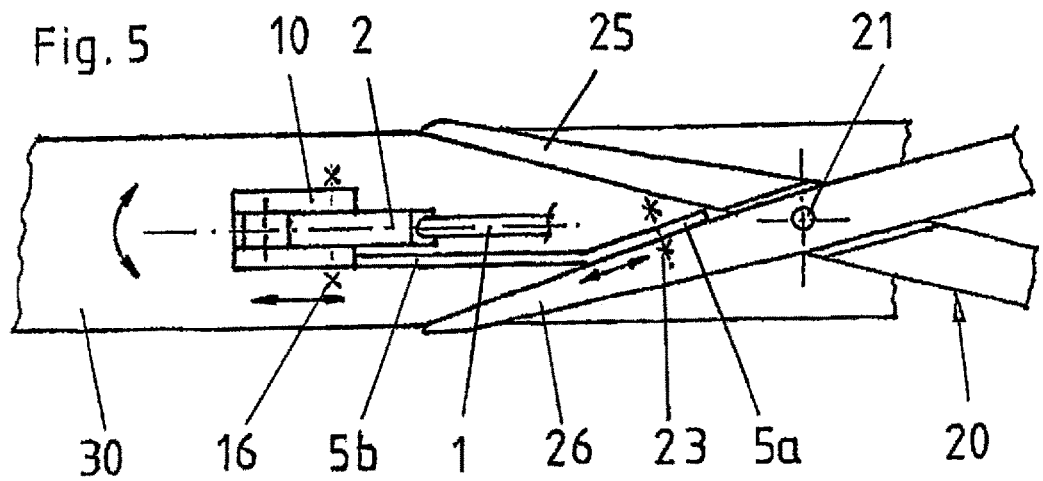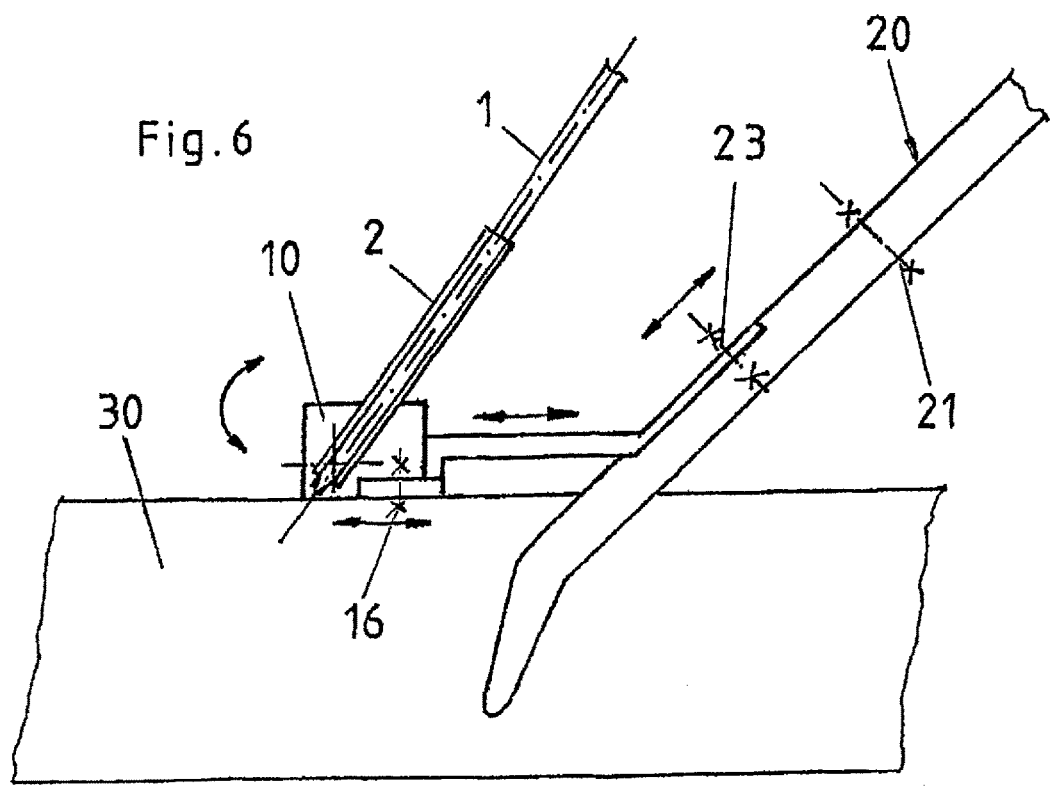

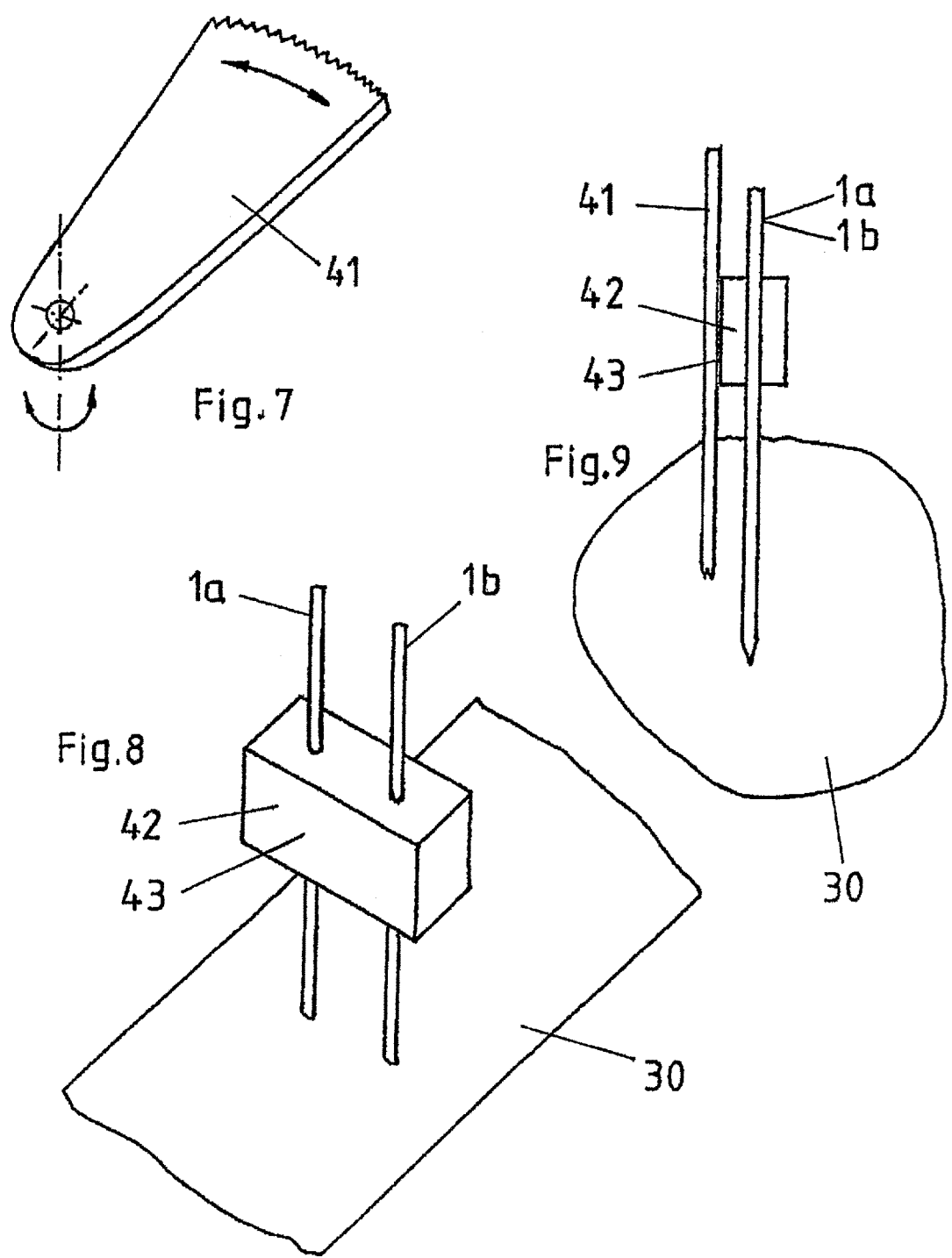

AIMING DEVICE

FIELD OF THE INVENTION

The present invention relates to an aiming device for insertion of one or more Kirschner-wires, a bone forceps provided with an aiming device, and a method for the application of an aiming device.

DESCRIPTION OF THE PRIOR ART

Minimal invasive operation practice is frequently performed in combination with cannulated screws in case of screw-osteosyntheses, e.g. at the proximal femur or at the pelvis. In this case a Kirschner-wire has to be correctly inserted in the bone through a puncture incision in the soft tissue. Only after the Kirschner-wires correct position is confirmed via intraoperative fluoroscopy the thick cannulated screw is screwed in over the previously correctly positioned Kirschner-wire.

From U.S. Pat. No. 4,341,206 "Device for producing a hole in a bone" published on 27.7.1982 a device for producing a hole in a bone is known. An aiming device with a plate is placed at a femur, said plate being in contact with the bone. By means of a handle the surgeon can rigidly urge the plate against the bone and determine the position of the plate. A guide tube, respectively a guide sleeve arranged at an angle has a bore hole wherein a Kirschner-wire may be inserted in a fitting manner. The position of the Kirschner-wire is verified by means of X-ray radiation. An adjustment of the entry angle of the Kirschner-wire is not possible in case of this device.

JP-A-200/000257 "Cup installation angle setter for artificial hip joint replacement arthroplasty" published on Jun. 28, 1996 discloses a further state of the art, wherein a fixation member for an aiming guide which contacts the bone is manually held. At this fixation member a tiltable guide sleeve for a Kirschner-wire is attached. Therewith the position of the guide sleeve and the entry angle of the Kirschner-wire relative to the bone is fixable.

CH-A-692023 "Instrument for percutaneous bone joint screw bonding" published on Jan. 15, 2002 discloses how two Kirschner-wires are positioned at a fixation device in one plane. At the same fixation device a mounting is attached via a ball-joint, whereby this mounting is provided with a guide sleeve for a further Kirschner-wire.

WO-A-0119265 "Repositioning device for bone fragments" published on Mar. 22, 2001 discloses a device for repositioning bone fragments at the pelvis or at tubular bones. The first clamping member abuts the bone. The second clamping member is provided with bore holes parallel to the first clamping member, said bore holes being suitable for receiving a Kirschner-wire.

DE-U1-20300988 "Drilling tool for bones, particularly for the proximal femur" published on Mar. 8, 2003 discloses a drilling tool, particularly for a proximal femur with a drill bit and a Kirschner-wire. The objective of this invention is that the surgeon can detect without X-ray verification if the Kirschner-wire jams during forwarding the drilling tool.

WO-A-98/04203 "Orthopaedic system allowing alignment of bones or fracture reduction" published on Feb. 5, 1998 discloses an instrument for alignment of an instrument with regard to a bone structure under virtual reality conditions. It can be used e.g. to insert a Kirschner-wire without trial drilling. This also allows to reduce the radiation exposure for the patient. The system consists of four parts: an aiming device, a calibrating device, a measuring device and a regulator. This permits a representation of the actual alignment status in two planes in virtual reality after e.g. X-ray images have been acquired and stored in a computer. The basis for this is that the instrument to be inserted can be exactly positioned with regard to its target if one aligns two planes at the body to be examined. The high measuring and computing effort appears disadvantageous in this embodiment.

JP-A-11/019095 "Positioning utensil for perforation for knee joint ligament bridging" published on Jan. 26, 1999 discloses a tube with a channel wherein a Kirschner-wire is guided. Furthermore, a handle is disclosed which is connected to one end of the tube and a securing device at the other end of the tube for fixation at a femur. The front end of the tube and the securing device for the femur are provided with a surface that prevents sliding.

JP-A-7/299079 "2 Row nail guide device for positioning of end screw hole of nail for mutual fixation" published on Nov. 14, 1995 discloses a two row nail guide device for positioning of screw holes and a tibia where adjustable rods are attached to. At one rod an eccentric guide sleeve for a Kirschner-wire is attached.

U.S. 2002/0099309 A1 "Kirschner-wire with a holding device for surgical procedures" published on Jul. 25, 2002 discloses a Kirschner-wire with a holding device. An aiming ring placed on an insertion device allows the placement of a Kirschner-wire using X-ray radiation.

Furthermore, from the state of the art in osteosynthesis forceps with springs for opening the legs of the forceps and with locking screws and locking ratchets for fixing the clamping forces are known. Examples for this can be found e.g. in the internet on the homepages of manufacturers of medical forceps.

In order to determine the correct spatial position of a Kirschner-wire in the body the Kirschner-wire has previously to be represented intraoperatively in at least two non-parallel planes of projection by means of fluoroscopy. Practically, the entry point and entry angle of the Kirschner-wire in the bone are already corrected under repeated radiation until the starting point and the direction of the bore holes are correct in both planes of projection.

For this purpose two C-arms can be simultaneously positioned around the patient. Alternatively, a single C-arm can be used in alternating planes of projection. As a matter of principle using a single C-arm results in the disadvantage that in case of a correct alignment of the wire in one plane a simultaneous check in the second plane is not possible. When the position and direction of the wires must be corrected in the second plane of projection no supervision is possible about the alignment in the first plane. The information concerning the position in the first plane is not automatically transferred into the second plane of projection each. Thus, the correct alignment of the Kirschner-wire requires an iterative procedure including numerous alternations of the plane of projection and repeated insertion of Kirschner-wires in slightly varied position. This can be cumbersome for the patient and time consuming for the surgeon.

SUMMARY OF THE INVENTION

It is a first object of the invention to provide an aiming device for the insertion of one or more Kirschner-wires and which is clampable to a bone by means of a forceps. Said aiming device comprising an aiming block for one or more Kirschner-wires, whereby said aiming block can be put against a bone and wherein said aiming block is connected to a fixing device, which is configured as a forceps clampable to a bone.

In a preferred embodiment the forceps comprise a securing function, preferably a ratchet fixation for the clamping legs of the forceps.

In another embodiment the forceps comprise handles or levers suitable for single hand use of the forceps.

In a further embodiment the aiming block is adjustable in a first plane E1 relative to a bone.

In again a further embodiment a guidance which is moveable in a second plane E2 is attached to the aiming block.

In still another embodiment the guidance for the Kirschner-wire is pivotable in the aiming block about an axis of rotation, which preferably cuts a longitudinal axis of the guidance.

In a further embodiment a frictional engagement is provided between the guidance and the aiming block, preferably in the range of the axis of rotation, so that the guidance is kept at a selected defined angle within the aiming block in a self-locking manner.

It is a second object of the invention to provide an aiming device for the insertion of one or more Kirschner-wires and which is provided with a pivotable guidance for said one or more Kirschner-wires. Said aiming device comprising an aiming block for one or more Kirschner-wires, whereby said aiming block can be put against a bone and wherein said aiming block is connected to a fixing device which is clampable to a bone. Furthermore, said guidance is pivotably attached to the aiming block.

In another embodiment the guidance for the Kirschner-wire is pivotable in the aiming block about an axis of rotation, which preferably cuts a longitudinal axis of the guidance.

In a further embodiment the aiming block is adjustable in a first plane E1 relative to a bone.

In yet a further embodiment the guidance is moveable in a second plane E2.

In still another embodiment a frictional engagement is provided between the guidance and the aiming block, preferably in the range of the axis of rotation, so that the guidance is kept at a selected defined angle within the aiming block in a self-locking manner.

In a further embodiment the fixing device is configured as a forceps with a securing function, preferably a ratchet fixation for the clamping legs.

In another embodiment the aiming block is adjustable in a third plane relative to a bone and the fixing device.

In yet another embodiment the first and second plane E1, E2 and preferably the third plane E3 are at an angle between 90° and 160° relative to each other.

In a further embodiment the aiming block is displaceable relative to the fixing device and parallel to the third plane E3.

In still a further embodiment the forceps comprise clamping legs which are preferably curved or cranked.

In another embodiment the forceps comprise clamping legs which are provided with rough or structured surfaces at their surfaces abutting a bone.

In a further embodiment the aiming block is attached to a rail, which is guided and fixable preferably in the range of the pivoting point of the clamping legs and particularly in a recess.

In still a further embodiment the rail is fixable at the forceps by means of a fixation means, preferably a knurled screw.

In another embodiment the aiming block is longitudinally and/or transversely displaceable and/or rotatable relative to the rail if necessary and fixable at the front end of the rail.

In a further embodiment the rail is guided in a rear section parallel to the forceps in the plane E3, and wherein the front section of the rail is configured at an angle W with respect to the rear section, whereby the angled proximal section is guidable parallel to the external contour of a bone.

In still a further embodiment the angle W is adjustable or fixed and is in a range between 90 and 160°, typically about 150°.

In another embodiment the aiming block and/or the guidance are made of a radiolucent material, preferably PEEK.

It is a third object of the invention to provide a bone forceps with a locking means, e.g. a ratchet fixation and clamping legs for abutment at a bone, whereby the bone forceps is provided with an aiming device for one or more Kirschner-wires.

In a further embodiment the aiming device comprises an aiming block and at least one guidance for at least one Kirschner-wire, said guidance being pivotable in the aiming block.

In another embodiment the aiming block is adjustable by means of a displaceable rail at the bone forceps.

BRIEF DESCRIPTION OF THE APPLICATION OF THE INVENTION

The preferred application is the exact positioning of Kirschner-wires, which are suitable as guiding elements for cannulated screws in the range of the proximal femur or at the pelvis.

At the beginning of the operation the Kirschner-wire is inserted in the aiming block, so that the tip of the wire is visible at the remote end of the bore hole of the guide sleeve.

Subsequently, the direction of the Kirschner-wire and of the aiming block as well is adjusted in the first plane of projection and checked by means of radiation perpendicularly to this plane and eventually corrected.

As soon as the direction of the Kirschner-wire is adjusted in the first plane the positioning in the second plane of projection is realised accordingly to the desired direction. Again the position of the Kirschner-wire should be checked by means of radiation and a navigation device and corrected, if necessary.

After being positioned by means of the aiming device the Kirschner-wire can be inserted in a positional correct manner and without further supervision.

In a preferred embodiment of the method for the use of a forceps with an aiming device the forceps are put against a bone so that the rail is approximately parallel to a bone. Subsequently the rail is displaced relative to the forceps in the direction of a bone such that the aiming block abuts the periost.

In another embodiment the aiming block is displaced and/or pivoted at the front section of the rail relative to the same and fixed.

In a further embodiment the guidance for the Kirschner-wire in the aiming block is tilted about its axis of rotation, respectively aligned by means of X-ray observation.

In yet a further embodiment an X-ray projection is provided perpendicularly to the first and second plane E1, E2 each in order to achieve an optimal alignment.

In another embodiment a navigation device is provided, by means of which the spatial position of the Kirschner-wire is determinable and displayable before insertion in a bone.

In a further embodiment the navigation device also comprises 2-3 markers M at a bone.

In yet a further embodiment markers M are also attached to the forceps and/or the Kirschner-wire.

In another embodiment markers M are attached to the forceps and also to the guidance for the Kirschner-wire.

ADVANTAGES OF THE SOLUTION ACCORDING TO THE INVENTION

Through avoiding repeated drilling due to mistaken positioning of the wire under similar angles a precise placement can be achieved. After repeated drilling with slightly altered angles in osteoporotic bones as in case of conventional procedures the Kirschner-wire disadvantageously might run into a an already produced drill channel due to low resistance such complicating or preventing a positional correct positioning. Due to the restriction to two planes of correction only the time of radiation and accordingly the exposure to radiation can be reduced.

A BRIEF DESCRIPTION OF THE DRAWINGS

FIG. 5 illustrates a top view on a bone with a forceps with aiming block;

FIG. 6 illustrates a lateral view on a bone with a forceps with aiming block;

FIG. 7 illustrates an oscillating saw blade for osteotomies;

FIG. 8 illustrates a saw block having a guide plane for an oscillating saw blade;

FIG. 9 illustrates a lateral view of a saw block with saw blade.

Figure 1:
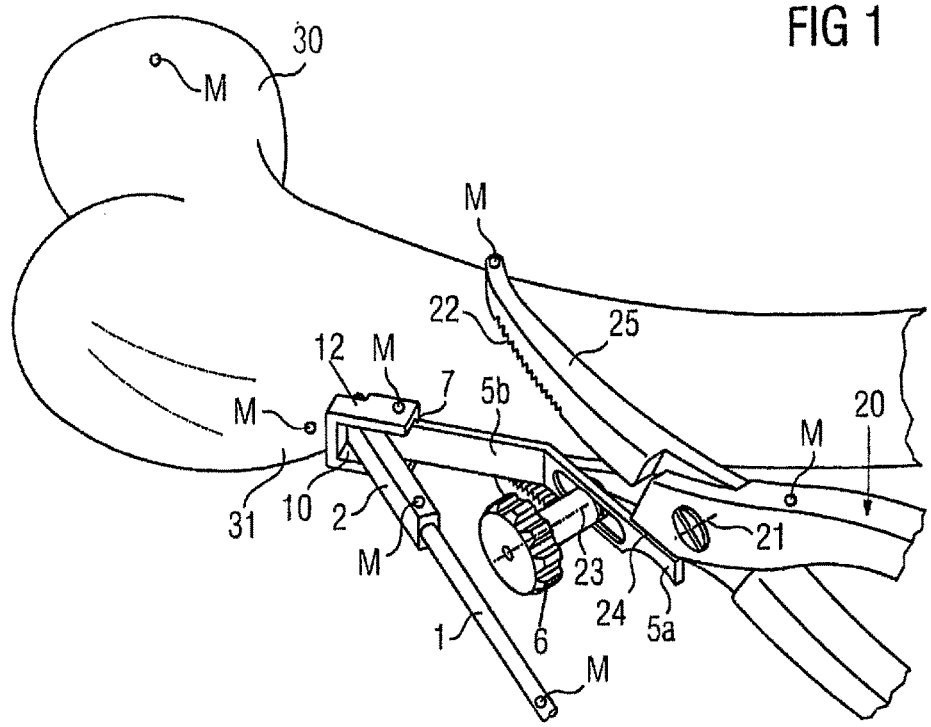
FIG. 1 illustrates an aiming device fixed at a femur.

The aiming device shown in FIG. 1 consists of a radiolucent central aiming block 10, material e.g. Polyetheretherketone (PEEK) with a high radiolucence, which is displaceably mounted at a forceps 20 (material e.g. instrument steel). The forceps 20 has clamping legs 25; 26 and is provided with a ratchet 22, so that the instrument is kept in its actual position when being clamped to a bone 30. In an exemplary way some markers M are shown in FIG. 1. These may be positioned at other locations or in another number as well.

Figure 2:
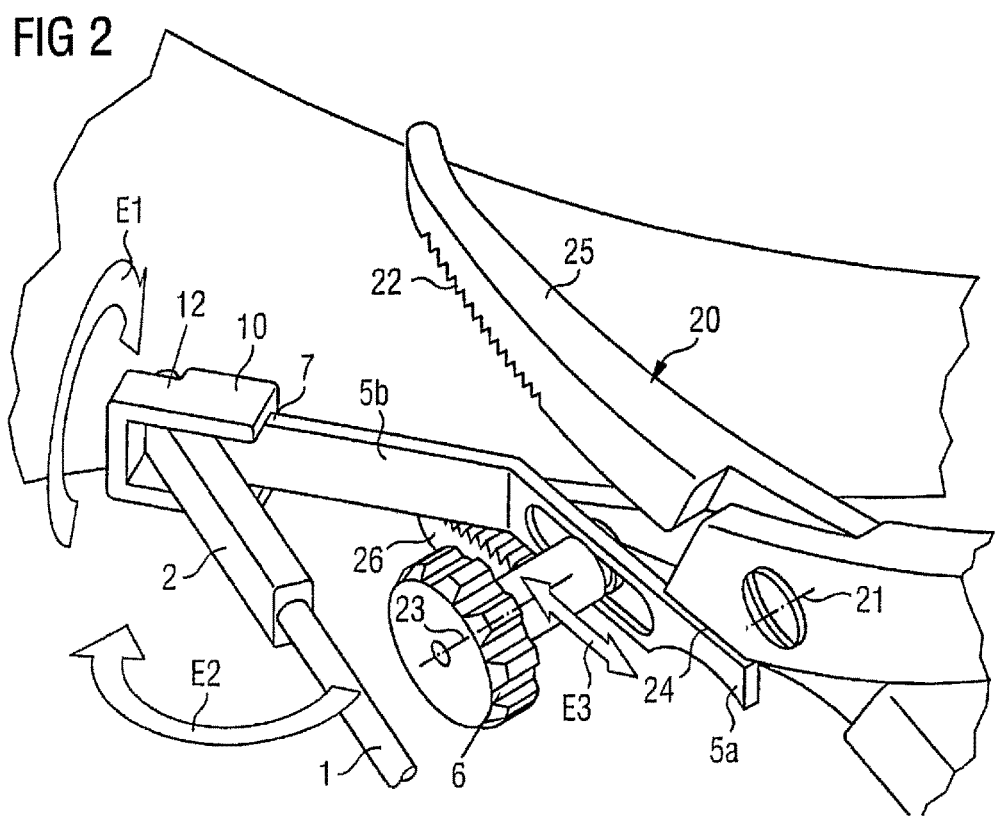
FIG. 2 illustrates the possible planes allowing positioning of the aiming device at a femur.

The fixation at the bone 30 may be varied, by closing the forceps 20 more or less powerfully. Principally, the spatial position of the forceps 20 with respect to the bone 30 is defined in all planes. By means of the knurled screw 6 (material e.g. instrument steel) in the range of the axis 23 of the forceps the aiming block 10 may be pushed on a rail 5 as far as the periosteum 31 and secured in two planes E1;E3 (see FIG. 2). The first portion 5a of the rail 5 lies on or is parallel to the line of intersection of the planes E2/E3, the second portion 5b of the rail 5 lies in the plane E2. The axis of rotation 12 in the aiming block 10 is defined with regard to its position relative to the bone 30 by means of the displacement of the rail 5.

Figure 3:
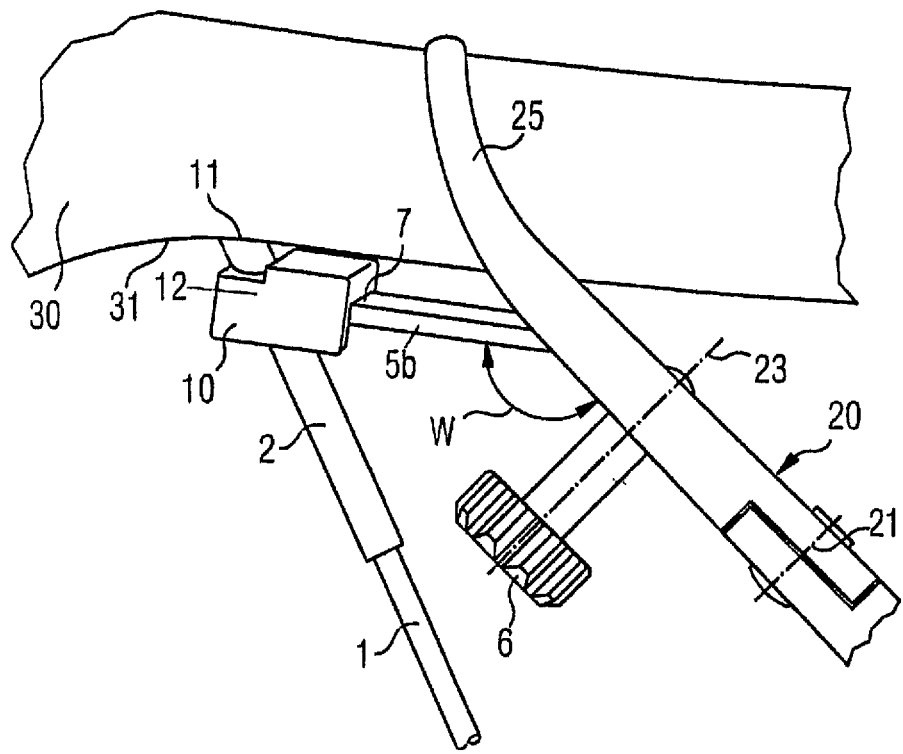
FIG. 3 illustrates a top view on the aiming device.

Before insertion of the Kirschner-wire 1 in the bone 30, its position and direction in two planes can be checked and adjusted by means of the path of the rays and a navigation device. The displaceability of the guidance 2 for the Kirschner-wire 1 is preferably self-locking. The rail 5 can be fixed by means of the knurled screw 6 in the range of the pivoting point 23 of the forceps. The guidance 2 for the Kirschner-wire 1 is pivotable about the axis of rotation 12. The remote end of the bore hole 11 of the guidance 2 of the Kirschner-wire 1 abuts the bone 30, whereby the tip of the Kirschner-wire 1 contacts the bone 30, see FIG. 3.

Figure 4:
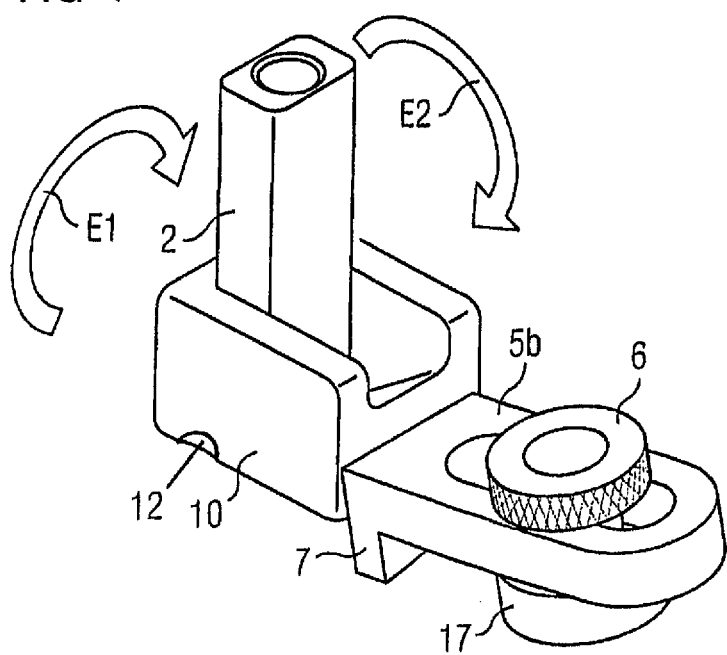
FIG. 4 illustrates a schematic representation of the aiming device.

FIG. 4 illustrates a schematic view of an aiming device for a fixation by means of bone screws 17. The guidance 2 for the Kirschner-wire 1 is pivotable in the plane E2 in the aiming block 10, the aiming block 10 is attached pivotably in the plane E1 at the end 7 of the rail 5b. The axis of rotation 12 is brought in contact close to the periost 31 of the bone 30.

FIGS. 5 and 6 illustrate schematic diagrams for a forceps 20 with a displaceably attached aiming block 10, whereby the aiming block 10 is displaceably connected with the forceps 20 via the rail sections 5a, 5b. The guidance 2 is pivotable in the aiming block 10. The aiming block 10 is pivotably as well as displaceably attached to the rail section 5b. For the fixation of the aiming block 10 locking screws 16 are used. Embodiments are imaginable which are not provided with a fixation, since the aiming block 10 e.g. is not pivotably configured.

A possibility for the application of the aiming device 15 is illustrated in FIGS. 7, 8 and 9. The aiming device 15 permits the matching insertion of Kirschner-wires 1a, 1b e.g. in the form that two Kirschner-wires are driven parallel in the bone 30. On these parallel Kirschner-wires 1a, 1b a saw block 42 is guided. The oscillating saw blade 41 is put against the guide planes 43.

It is advantageous for the function according to the invention that in case of each X-ray projection the path of the rays is perpendicular to the respective plane E1, E2 of the aiming block.

Only after having the aiming block 10 in a desired alignment the Kirschner-wire 1 is inserted in the bone 30. Such only one perforation of the bone 30 is necessary.

The navigation device comprises—as commonly known—also 2-3 markers M at the bone 30.

Markers M are also attached to the forceps 20, to the Kirschner-wire 1 and also to the aiming block 10 and/or to the guidance 2 for the Kirschner-wire 1. The navigation device is configured such that it detects the markers thus allowing a mutual spatial allocation of the parts relative to the bone. By means of this allocation the computer can subsequently generate a virtual representation of the Kirschner-wire in the bone, allowing to visualize its final position already before the wire is inserted.

By means of the clamping effect of the forceps 20 the navigation markers M are fixed, and with two markers M at the guidance 2 and/or at the Kirschner-wire 1 the direction of the Kirschner-wire 1 is then exactly determinable.

The guidance for the Kirschner-wire 1 can also be configured multipart, such comprising guide bores e.g. for two or more Kirschner-wires. Two or more guidances 2 could be mounted in a parallel manner at the aiming block 10, so that two or more Kirschner-wires could be inserted in the bone correctly positioned and in a mutual spatial allocation simultaneously or subsequently via one or more alignments. This can be useful in case where e.g. the bone has multipart fragments which must be connected to each other or when the Kirschner-wires are not to be used for cannulated screws but as a guidance for other tools, e.g. for saws for the osteotomy. In such a case a displaceable guidance as a saw holding guidance might be mounted to the Kirschner-wires, whereon a saw can be guided in a longitudinally displaceable manner relative to the Kirschner-wires. Particularly, the saw holding guidance can be configured as a block with two parallel guide bores for Kirschner-wires 1. These parallel guide bores would then be approximately congruent with the two guidances 2 in the aiming block 10.

In an advanced development of the invention the aiming block 10 itself is used as a saw holding guidance, whereby the guidances 2 mutate to the guide bores of the block. In this embodiment the aiming block 10 is removable as a whole from the rail 5b and is subsequently displaceable parallel in the direction of the previously inserted Kirschner-wires 1.

What is claimed is:

1. An aiming device for insertion of a Kirschner-wire to treat a target bone, comprising:
   an aiming block permitting placement of a Kirschner-wire against the target bone; and
   a forceps connected to the aiming block, the forceps being configured to clamp to the target bone, wherein the aiming block can be put against the target bone while the forceps is clamped to the bone.

2. The aiming device according to claim 1, wherein the forceps comprise a ratchet mechanism fixing legs thereof in a desired clamping position on the bone.

3. The aiming device according to claim 1, wherein the forceps comprise a plurality of levers enabling single handed use thereof.

4. The aiming device according to claim 1, wherein an orientation of the aiming block relative to the bone is adjustable in a first plane.

5. The aiming device according to claim 1, further comprising a guide member attached to the aiming block, the guide member being moveable relative to the aiming block in a second plane.

6. The aiming device according to claim 5, wherein the guide member is configured to receive a Kirschner-wire and is pivotable within the aiming block about an axis of rotation.

7. The aiming device according to claim 6, wherein the axis of rotation passes through a longitudinal axis of the guide member.

8. The aiming device according to claim 5, further comprising a frictional engagement mechanism between the guide member and the aiming block self-locking the guide member at a predefined angle relative to the aiming block.

9. An aiming device for insertion of a Kirschner-wire to treat a target bone, comprising:
   a) an aiming block permitting placement of a Kirschner-wire against the target bone;
   b) a guide member pivotally coupled to the aiming block, the guide member configured to receive the Kirschner-wire; and
   c) a fixing device coupled to the aiming block, the fixing device configured to clamp to the target bone to maintain the aiming block in a desired position relative to the target bone, wherein the aiming block can be put against the target bone while the fixing device is clamped to the bone, wherein the fixing device comprises a forceps.

10. An aiming device for insertion of a Kirschner-wire to treat a target bone, comprising:
    a) an aiming block permitting placement of a Kirschner-wire against the target bone;
    b) a guide member pivotally coupled to the aiming block, the guide member configured to receive the Kirschner-wire; and
    c) a fixing device coupled to the aiming block, the fixing device configured to clamp to the target bone to maintain the aiming block in a desired position relative to the target bone, wherein the aiming block can be put against the target bone while the fixing device is clamped to the bone,
    wherein at least one of the aiming block and the guide member is made of a radiolucent material.

11. The aiming device according to claim 10, wherein the at least one of the aiming block and the guide member made of a radiolucent material is formed of PEEK.

* * * * *